United States Patent [19]
Verma

[11] Patent Number: 5,374,557
[45] Date of Patent: Dec. 20, 1994

[54] FERMENTATION VESSELS AND CLOSURES THEREFOR

[76] Inventor: Kuldeep Verma, 3509 Crofton Ct., Raleigh, N.C. 27604

[21] Appl. No.: 55,506

[22] Filed: Apr. 29, 1993

[51] Int. Cl.$^5$ .................. C12M 1/24; C12M 61/00; B65D 51/16
[52] U.S. Cl. .................. 435/296; 435/286; 435/284; 422/102; 215/307; 215/336; 215/344; 220/366; 220/373; 220/374
[58] Field of Search ............ 435/284, 285, 286, 296; 422/102, 101, 99; 215/307, 308, 336, 344; 220/236, 366, 373, 374

[56] References Cited
U.S. PATENT DOCUMENTS

| | | | |
|---|---|---|---|
| 2,562,010 | 7/1951 | Aitken | 220/366 |
| 3,927,798 | 12/1975 | Loomis | 220/374 |
| 4,600,112 | 7/1986 | Shillington et al. | 215/274 |
| 5,067,624 | 11/1991 | Thanisch | 215/235 |

*Primary Examiner*—David A. Redding
*Attorney, Agent, or Firm*—Olive & Olive

[57] ABSTRACT

A closure device for fermentation test tubes or flasks (vessels) comprises a cylindrical cap which is either molded integrally with the vessel as one piece or is molded separately and is snugly fitted over the neck of the vessel, in a fashion which not only allows for free gaseous flow between the contents of the vessel and the ambient atmosphere but also facilitates easy access to the contents of the vessel without having to detach the closure from the vessel. Particular features of the cover permit manipulation with the fingers of the hand holding the vessel.

14 Claims, 5 Drawing Sheets

FERMENTATION VESSELS AND CLOSURES THEREFOR

BACKGROUND OF THE INVENTION

1. Field of the Invention

The present invention relates to fermentation vessels and closure devices for such vessels. More particularly, the present invention concerns fermentation vessels and specifically to fermentation vessels having closure devices which permit easy access to the vessel contents and also allow free exchange of gases between the contents and the ambient atmosphere.

2. Background of the Art

Fermentation processes, particularly cell or tissue culture procedures, are employed in a wide variety of research activities ranging from textiles to pharmaceuticals. Biotechnology research makes extensive use of fermentation procedures, which in general involve growth of a single purified strain of micro-organism with a goal of obtaining more cells or purifying the byproducts. The isolation of pure strains of microorganisms is a detailed process involving many steps. A newly identified colony of a particular microorganism is first transferred from a petri dish culture to a separate vessel containing appropriate nutrients. This microorganism is typically transferred several times to a new petri dish or a culture tube until the culture is free of contamination by other undesired strains of microorganisms. After purification of the strain, one needs to study the nature of this newly isolated strain of microorganism. For this purpose, one needs to grow it in a selected medium. The medium is inoculated with the microorganisms and placed in an incubator with a rotary shaker at a suitable temperature and for a period of time sufficient to permit growth of the microorganism culture. New nutrients or chemicals are added to the actively growing culture to impose selection pressure, or the new microorganism is sampled many times through the growth period for analysis and the consumed quantity of the nutrient medium is replenished. These operations require inoculation of a culture in the vessel by means of a sterile inoculation loop inserted through the mouth of the culture vessel so as to touch the medium inside. Similarly, sampling of the contents during the growth period requires introduction of sterile sampling devices into the active culture. Good laboratory practice dictates that all apparatus involved with a procedure viz. the closure, the vessels the inoculation loop and the samplers must be sterile to avoid contamination by exogenous microorganisms. All of these operations according to known practice, require manipulation of the vessel, the closure and a transfer loop or pipette with interchanging of functions involving both of the worker's hands. This process is cumbersome and needs lot of experience to accomplish without error, particularly when one has to handle multiple vessels. The vessel is typically in the form of a test tube or flask.

With the prior art type of vessel, the worker has to perform the following series of operations for each vessel:

(i) lift the vessel from the rack with a first hand;
(ii) remove the cap with second hand;
(iii) keep the cap somewhere in the work area which itself must be kept sterile;
(iv) pick up the inoculation or sampling device with a second hand:
(v) perform inoculation or sampling, as the case may be:
(vi) set the sampling device down to make second hand free;
(vii) look for the same cap to avoid cross contamination;
(viii) replace the cap carefully; and
(ix) place the vessel back in the rack.

The vast majority of microorganisms useful in commercial viable fermentation processes are aerobic microorganisms; that is, microorganisms which require oxygen to carry on their metabolic processes. In fact, the very purpose of shaking or stirring fermentation broths is to ensure effective mixing of air with the liquid culture medium. As a result, any closure device employed in the culturing of aerobic microorganisms must permit the passage of air into the vessel and the discharge of gaseous fermentation byproducts from the vessel while maintaining the sterility of the vessel contents.

In the past it has been the widespread practice to close the fermentation vessel with porous closures such as a sterile cotton plug or a synthetic material such as foamed polyethylene or styrene etc. More recently, stainless steel and plastic cap closures have become available which fit over the mouth of the fermentation vessel and permit the passage of gases into and out of the fermentation vessel. Examples of such closures are KIM-KAP closures and KAP-UTS plastic closures available from Owens-Illinois and BELLCO stainless steel closures available from Bellco Technology. These closures each have an internal diameter slightly larger than that of the neck of the fermentation vessel and fit snugly over the vessel mouth by means of fingers or ridges on the inside vertical walls of the closures. Small fins inside the closure prevent the top of the closure from seating against the top of the fermentation vessel, thus permitting the passage of gases into and out of the vessel while maintaining the sterility of the vessel contents.

A disadvantage of these prior art closures, whether of the porous plug type or the snug fitting cap closure type, is the need to completely detach the closure in order to gain access to the fermentation vessel contents. Each removal of the closure provides the potential for contamination of the vessel contents and requires flaming or other sterilization treatment of the vessel mouth and closure to ensure sterility which adds to the amount of work required of the laboratory technician per unit vessel. A further style of prior art closure for a fermentation vessel is disclosed in U.S. Pat. No. 5,116,758 to the present inventor for a FERMENTATION VESSEL CLOSURE. The prior '758 patent addresses certain of these problems, but leaves others unresolved.

Thus, there is a need in the fermentation art for efficient fermentation vessels and closure devices which not only permit easy and direct access to the fermentation vessel contents without the need to remove the closure device but also allow for gaseous exchange.

Therefore, it is the principal object of the invention to provide a one piece closure, all portions of the closure being integral with each other and which may be opened and closed with the hand holding the vessel typically in the form of a test tube or flask.

Another object of the invention is to provide a fermentation vessel which can be molded integrally with an easily opened and closed closure cap.

Another object is to provide a fermentation vessel having a closure which permits easy access to the vessel contents and allows gaseous exchange.

The foregoing and other objects will become apparent as the description proceeds.

SUMMARY OF THE INVENTION

The present invention provides a new type of closure device for fermentation vessels which permits access to the contents of the vessel without requiring complete removal of the closure and further permits the passage of gases into and out of the vessel while maintaining the sterility of the contents. In one embodiment, an outer cylinder member of greater diameter than the outer diameter of the neck or mouth of the vessel is molded, integral with the vessel as one piece, with intervening space maintained by ridges running along the inside length to allow for gases to flow. The outer cylinder member bears a movable closure at the capping end. Alternately, the closure device of this invention may comprise a separate closure having a cylindrical wall portion open at one end and having at the other end thereof a cover. Means for engaging the mouth of a fermentation tube or flask are disposed along the inner surface of the cylindrical wall portion and stand off means for permitting the free flow of gases into and out of the capped fermentation vessel are disposed radially around the inner surface of the capping end. In this embodiment, the closure device is molded separately from the vessel.

The novelty and improvement in the fermentation vessel and closures of the present invention permit both gaseous exchange between the vessel contents and the outer atmosphere as well as free access to the fermentation vessel contents without requiring removal of the closure device. Furthermore, the closure is permanently molded and or snugly fitted to the container, so that one has only to deal with a pivotable or slidable cover at the capping end.

For purposes of comparison, with the new fermentation vessel closures described herein, one has to only perform these steps:

(i) lift the vessel from the rack with a first hand (actually this is not necessary in some applications e.g. in inoculation only);

(ii) open the lid of the closure using thumb or pointer finger of the first hand (the closure need not be removed and cannot be removed when it is molded as one piece with the vessel);

(iii) pick up the inoculation or sampling device with the second hand:

(iv) perform the inoculation or sampling; and (v) close the vessel with the finger of the first hand.

This simplified procedure avoids a lot of confusion since the worker can use only one hand to take care of the culture vessel and his other hand to deal with the inoculation or sampling device and with the operations,

DETAILED DESCRIPTION OF THE INVENTION

The fermentation test tube or flask incorporating the closure device of the invention permits covering of such a fermentation vessel so as to maintain the pre-established sterility of the contents while permitting access to the interior thereof to add to or remove from the vessel contents. The closure device establishes access through a one-hand manageable cover which permits transfer loops, pipettes and the like to be inserted into the fermentation vessel without removing the entire closure device. The closure device of this invention may be molded separately or integral with the fermentation vessel by conventional techniques well known in the molding arts of any suitable flexible resin which is capable of withstanding the temperatures required for autoclave sterilization. Suitable materials include synthetic polymers such as polyethylene, polypropylene, poly (tetraflouroethylene), polycarbonate, synthetic rubber and the like. A number of embodiments are illustrated and described below.

The closure of the present invention provides the convenience to the user of being able to hold the neck of a fermentation vessel and quickly and easily open (and close) the closure device using the finger or thumb of the hand holding the fermentation vessel and to carry out sampling or addition operations with the other hand. This one-hand capability simplifies the cumbersome procedure, associated with the prior art practice, of having one hand just for completely removing the closure to access the vessel contents and also to carefully place the detached closure in some sterile place to avoid contamination and, moreover, with a caution that the same closure has to be returned to the vessel to avoid cross contamination. Thus, while one hand just holds the fermentation vessel, the other hand has to do many operations. i.e., opening the closure, placing it in a sterile place, picking up the transfer loop or pipette for the required operation to be performed, releasing the loop or pipette to set this hand free for picking up the closure and closing the vessel. Thus, the existing closures are prone to risks of contaminations and errors and demand a lot of attention of the technician.

Figures 1, 2:
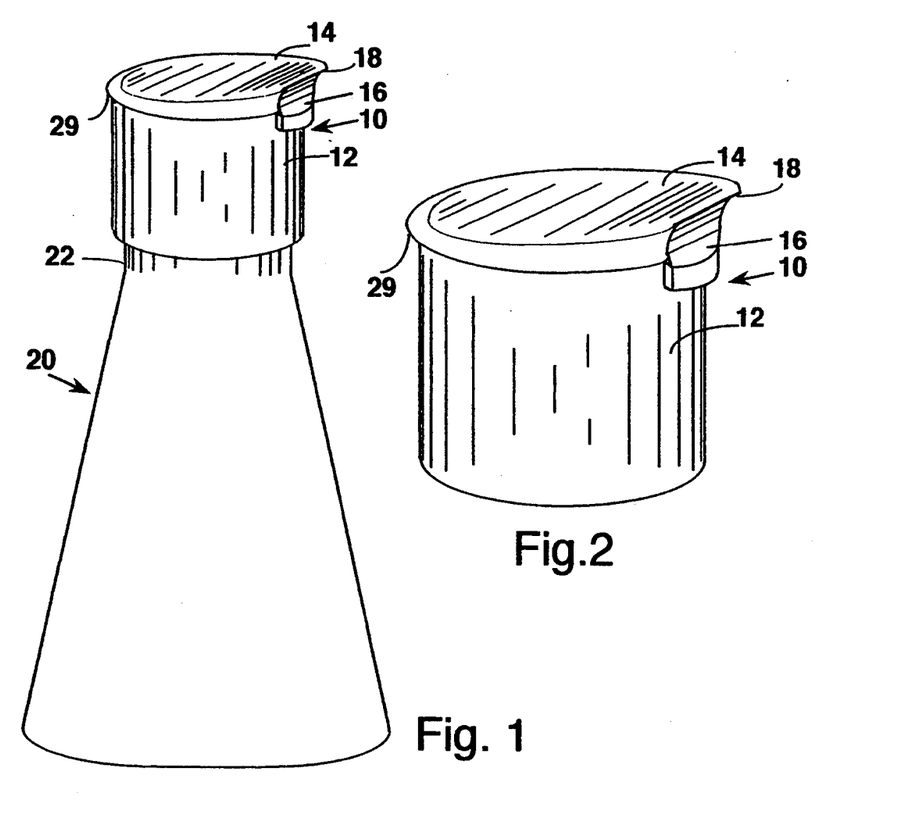
FIG. 1 is a perspective view of a fermentation vessel with a closure in accordance with a first embodiment of the present invention.
FIG. 2 is a perspective view of the fermentation vessel closure of FIG. 1 in the closed condition with the vessel not being shown for purposes of illustration.
Figure 2A:
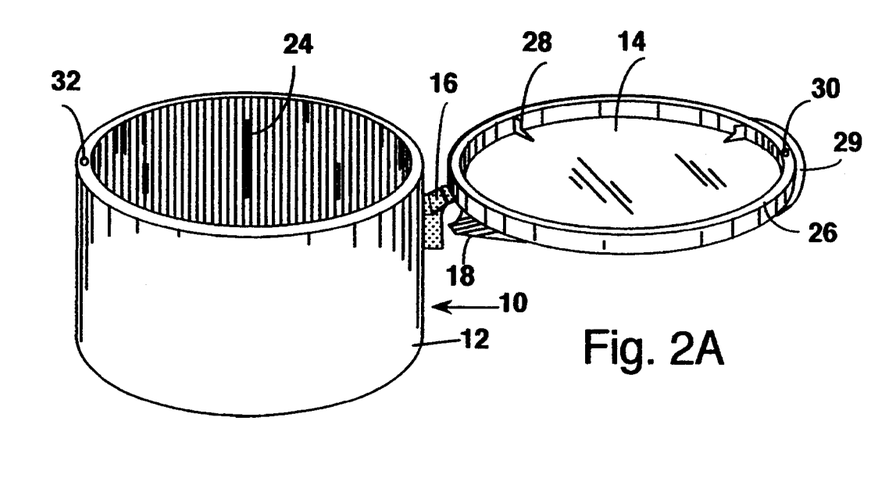
FIG. 2A is a perspective view of the fermentation vessel closure of FIG. 1 in the open condition with the vessel not being shown for purposes of illustration.

According to the previously discussed objectives and advantages of the present invention, a first embodiment thereof is illustrated in FIGS. 1, 2, 2A, 3, 4 and 4A. The primary unique advantage common to all embodiments of the invention is the ability of a user to open and close a closure cover with a single hand, thus leaving the second hand to perform other functions and while permitting the desired gas exchange. In FIG. 1, the separately molded closure 10 of the invention is shown mounted on a typical vessel, flask 20 having a neck 22. Collar 12 of closure 10 is attached to and closed by cover 14 by means of integral hinge 16 which is openable by a lever 18. An alternate opening structure is provided by lifter tab 29.

Figures 3, 4:
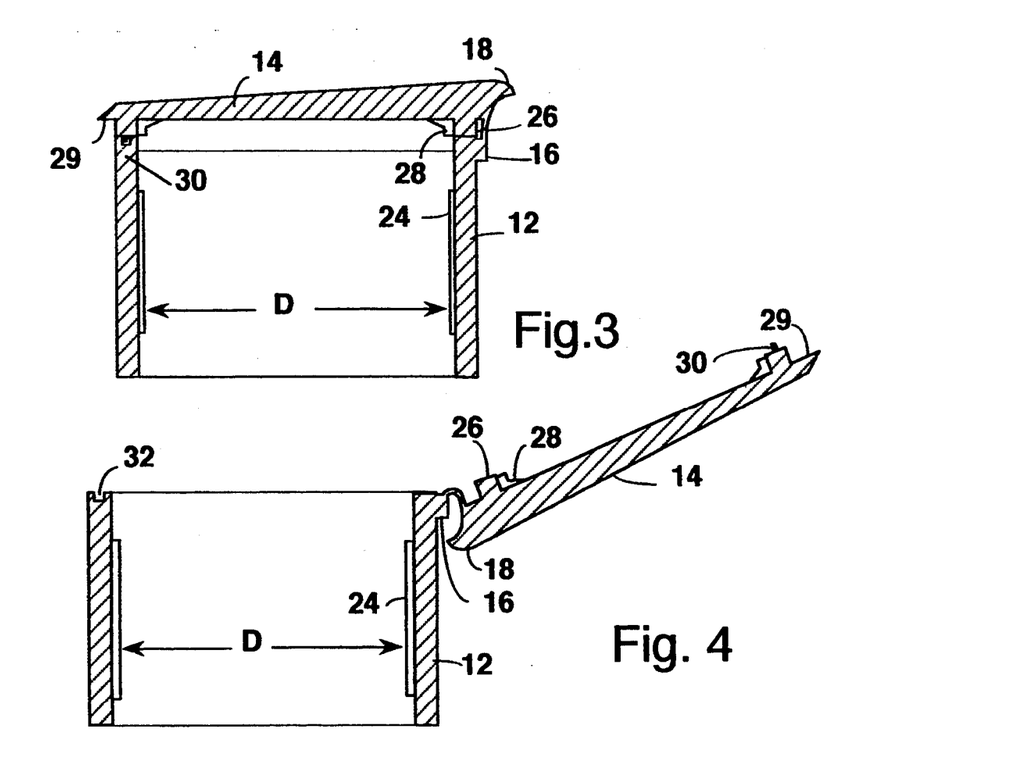
FIG. 3 is a cross sectional elevation view of the closure of FIG. 1 in the closed condition but with the vessel not being shown for purposes of illustration.
FIG. 4 is a cross sectional elevation view of the closure of FIG. 1 in the open condition but with the vessel not being shown for purposes of illustration.
Figure 4A:
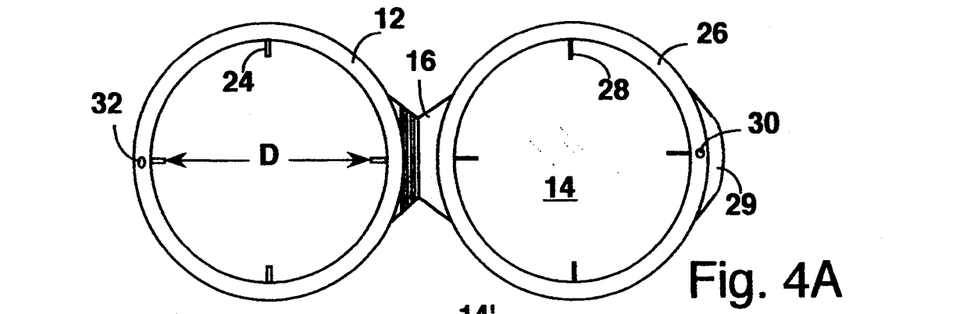
FIG. 4A is a top plan view of the closure of FIG. 1 but with the vessel not being shown for purposes of illustration.

Closure 10 is shown alone in FIG. 2 in perspective view, in FIG. 3 in cross sectional elevation as a closed unit, and in FIG. 4 as an open unit. In reference to the cross sectional views of FIGS. 3 and 4, and to views 2A and 4A, internally radiating standoffs 24 are dispersed about the inner circumference of collar 12 and terminate at a diameter D adapted to snugly fit over neck 22 of vessel 20 and maintain collar 10 in a selected position. Standoffs 24 serve to establish a series of gas exchange channels between neck 22 and collar 12 which is a relatively long and indirect path to minimize the chance of contamination. Cover 14 has a cover lip 26 of an essentially equal diameter to that of collar 12 and further has spacers 28 in a plurality of locations around the inner surface of cover 14 and adapted to keep cover 14 from sealing against the top of vessel 20 to permit the passage of air or other gases. Vessel 20 may be either a flask, test tube or other related laboratory container which is typically used in the intended process of culture fermentation.

It is preferred that the molding of closure 10 be accomplished in a manner so as to result in cover 14 being biased to remain open. Thus, when a laboratory technician presses down on the top of lever 18 or lifts tab 29 of closed cover 14, cover 14 springs to the open position. When the technician presses the top of cover 14 to a closed position, a lock pin 30 releasably engages a recess 32 to maintain cover 14 in the closed position, with spacers 28 keeping cover 14 from sealing against gas interchange.

Figure 5:
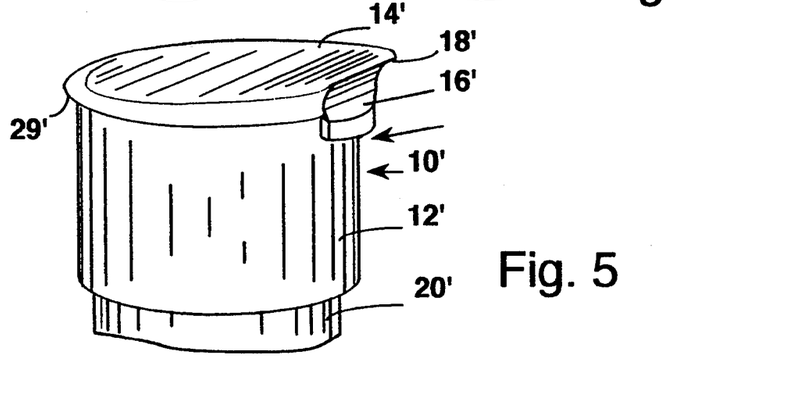
FIG. 5 is a perspective view of the fermentation vessel closure integrally molded with a partially illustrated fermentation vessel according to a second embodiment of the invention.
Figures 5A, 6:
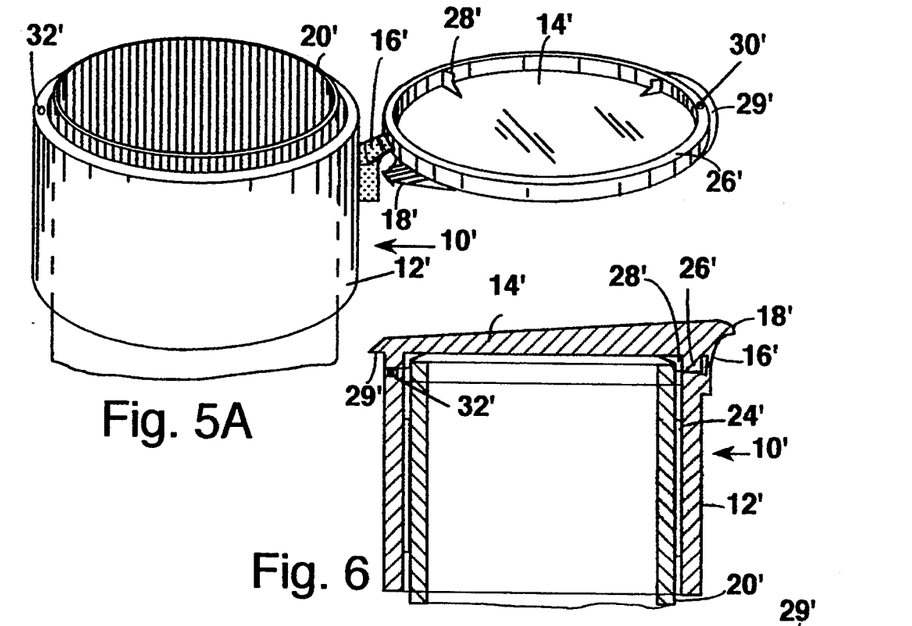
FIG. 5A is a perspective view of the closure and integrally molded vessel of FIG. 5 in the open condition.
FIG. 6 is a cross sectional elevation view of the closure and vessel of FIG. 5 in the closed condition.
Figure 7:
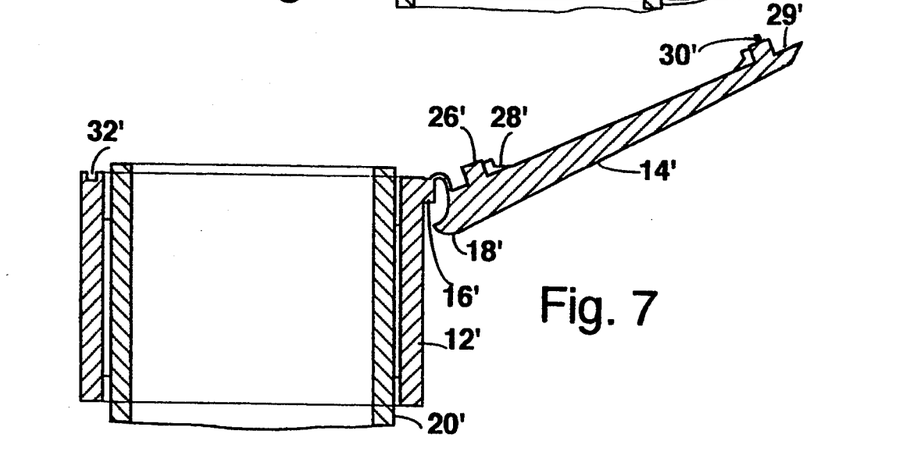
FIG. 7 is a cross sectional elevation view of the closure and vessel of FIG. 5 in the open condition.
Figure 7A:
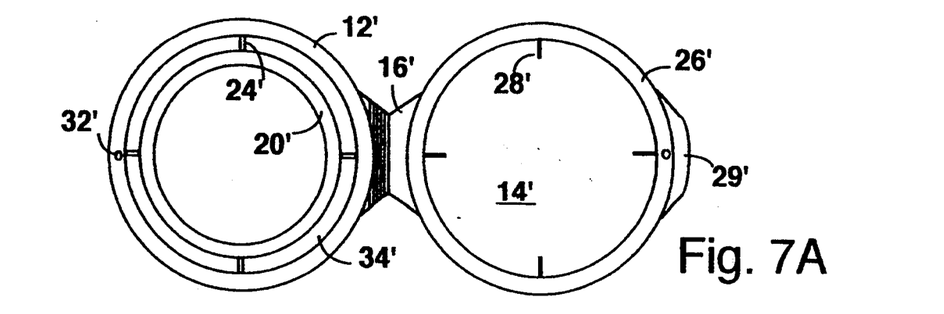
FIG. 7A is a top plan view of the closure and vessel of FIG. 5 in the open condition.
Figure 8:
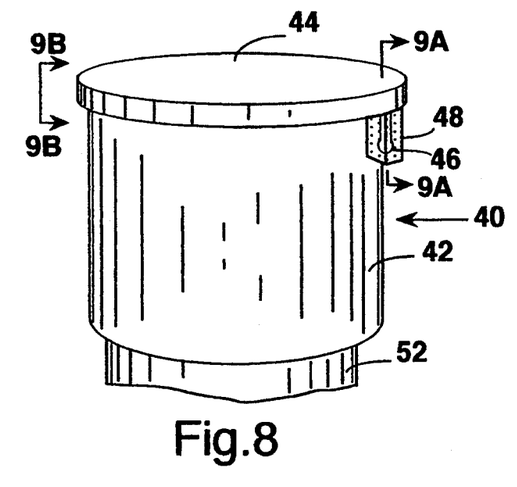
FIG. 8 is a perspective view of a fermentation vessel closure integrally molded with a partially illustrated fermentation vessel according to a third embodiment of the invention.
Figure 9A:
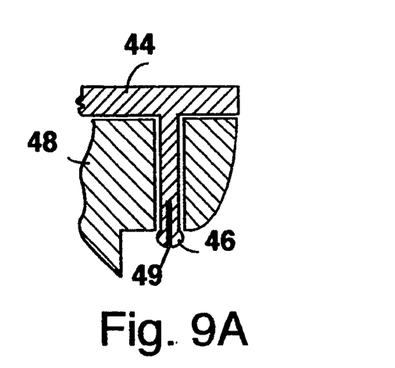
FIG. 9A is a partial cross sectional view taken in the direction of line 9A—9A of FIG. 8.
Figure 9B:
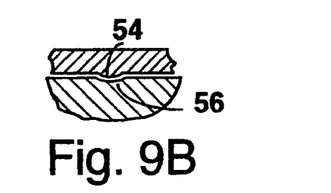
FIG. 9B is a partial cross sectional view taken in the direction of line 9B—9B of FIG. 8.
Figure 10:
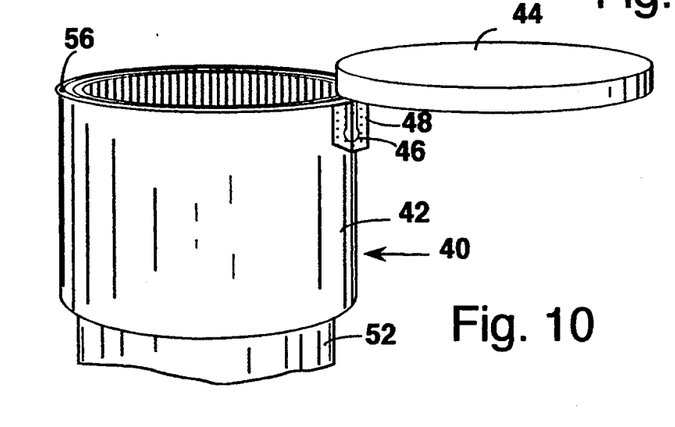
FIG. 10 is a perspective view of the closure and vessel of FIG. 8 in the open condition.

A different, but related second embodiment of the present invention is depicted in FIGS. 5, 5A, 6, 7 and 7A. The structure of the closure 10' of the second embodiment is similar to that discussed above, with the addition that closure 10' is molded integrally with the neck of vessel 20'. Thus, the closure and vessel become an integrally molded unitary structure. As shown in FIGS. 5A and 7, vessel 20' protrudes slightly above the top of collar 12' to allow more reliable and cleaner insertion of specimens and tools to the interior of vessel 20'. An air/gas channel 34 (FIG. 7A) is maintained between the respective walls of vessel 20' and collar 12' as is needed in carrying out an aerobic fermentation process.

FIGS. 8-14 are directed to two additional embodiments which operate differently than the first and second embodiments. According to the third embodiment, shown in respective closed and open views in FIGS. 8-10, collar 42 is integrally molded with vessel 52. Cover 44 is rotatably attached to the upper end of collar 42. Cover 44 is moved from the closed position (FIG. 8) to the open position (FIG. 10) by movement of a finger of the hand holding vessel 52 by pivoting around hinge pin 46. Detail of the assembly of hinge pin 46 integrally molded with cover 44 to collar 42 by means of boss 48 is shown in FIG. 9A. Pin 46 is molded with a snap-fit slotted end 49 as shown for simple assembly. Cover 44 is kept from accidental opening by the engagement of teeth 54 and depressions 56 as seen in FIG. 9B. In this embodiment, the upper end of collar 42 is equal to or higher than the height of vessel 52, and similar standoffs and air/gas channels are formed as those described above.

Figure 11:
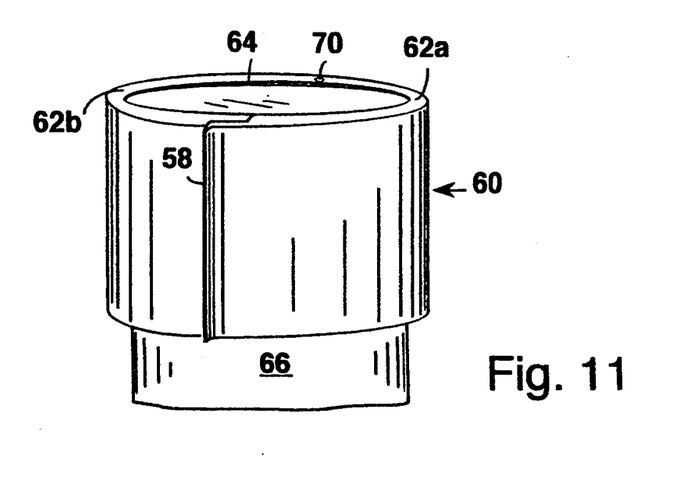
FIG. 11 is a perspective view of a fermentation vessel closure integrally molded with a partially illustrated fermentation vessel according to a fourth embodiment of the invention.
Figure 12:
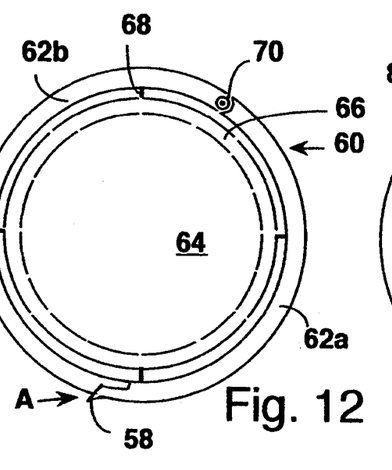
FIG. 12 is a top plan view of the closure and vessel of FIG. 11 in the closed condition.
Figure 13:
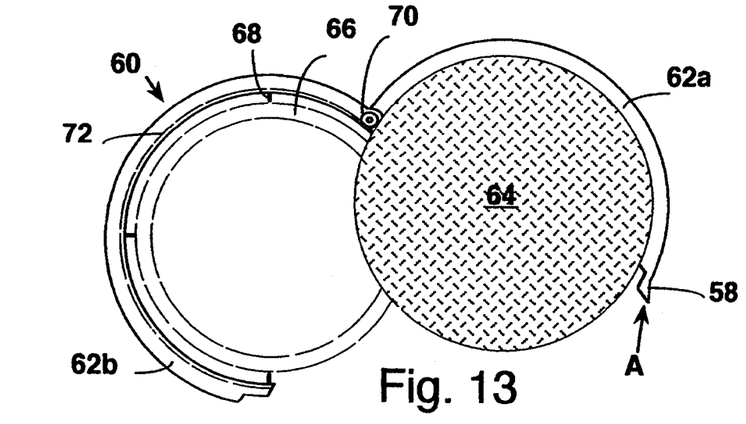
FIG. 13 is a top plan view of the closure and vessel of FIG. 11 in the open condition.

The fourth embodiment for exclusive use in aerobic fermentation is shown in FIGS. 11-13. In this case, collar 62 is divided into portions 62a and 62b. Fixed collar portion 62b is molded integral with, or subsequently adhered to, vessel 66; pivotal collar portion 62a is molded integrally at its upper end with cover 64 and assembled to fixed collar portion 62b by hinge pin 70. Collar portion 62b is formed with an undercut groove 72 adapted to receive the mating edge of cover 64 so as to minimize air infiltration and contamination. Tab 58 protrudes from the cylindrical contour of collar 62a, 62b as an aid in opening, as illustrated at arrow A in FIGS. 12 and 13.

Figure 14:
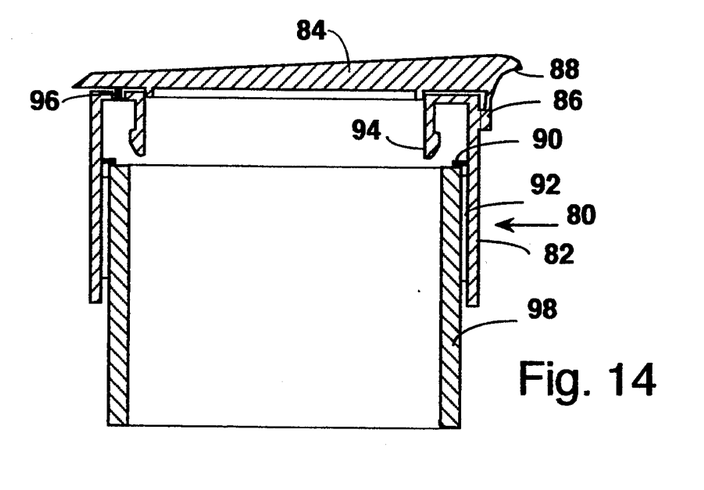
FIG. 14 is a cross sectional elevation view of a fermentation vessel closure according to a fifth embodiment of the invention and mounted onto a vessel neck.
Figure 15:
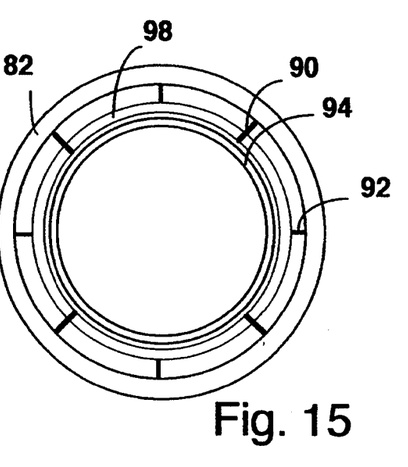
FIG. 15 is a bottom plan view of the closure of FIG. 14.

Whereas the embodiments described above relate to uses in aerobic fermentation, there is also a need for a closure for a fermentation vessel in an anaerobic process which closure is manipulable with a single hand. The fifth embodiment illustrated in FIGS. 14 and 15 is adapted to function with either aerobic or anaerobic culture techniques. Closure 80 is formed as a separate unit from test tube, flask or other vessel 98 so as to be able to mount in two significant positions relative to the condition of air/gas passage. Stand off 92 is formed as previously described in a plurality of positions radially around the inside surface of collar 82. At approximately the upper end of the stand offs 92, a series of flexible stops 90 are formed which protrude radially inwardly so as to contact the upper edge of vessel 98. When closure 80 is pressed onto the neck of vessel 98, stops 90 control the depth of engagement without blocking air/gas flow. In this mode, closure 80 allows air/gas flow and operates aerobicly as the earlier embodiments. If anaerobic processing is needed, further downward pressure on closure 80 will cause flexible stops 90 to yield and allow seal ring 94 to engage the inner surface of vessel neck 98 and prevent air/gas passage. Opening and closing is accomplished by manipulation of lever 88 about integrally formed hinge 86. A lock 96 to ensure the maintenance of a sealed condition of cover 84 is formed as disclosed in relation to the first and second embodiments of the invention.

In all embodiments, there is provided an improved fermentation vessel having a closure which, while permitting gas exchange, also permits easy access to the vessel contents and opening and closing by one hand manipulation.

While the invention has been described in terms of a series of specific embodiments, it is understood that these are intended as examples and not as limitations on the principles and scope of the invention. Further modifications and variations may be apparent to those skilled in the art, and the breadth of the invention is defined by reference to the claims which follow.

What is claimed is:

1. A closure for a fermentation vessel adapted for use in an aerobic procedure, comprising:
    (a) a cylindrical tubular member with a first and a second open end and having an inside diameter adjacent said first open end greater than the outside diameter of the neck of said fermentation vessel on which said cylindrical member is to be mounted;
    (b) a plurality of stand-off members spaced around the inside surface of and integrally molded with said cylindrical member and extending radially inwardly to a diameter adapted to snugly fit over the outside diameter or said neck of said vessel;
    (c) a cover pivotably attached to said cylindrical tubular member adjacent said second open end so as to be moveable between a closed position and an open position; and
    (d) means to support said cover so that a space is maintained between said cover and an upper end of said vessel neck so as to allow a gas to freely pass between the interior and the exterior of said vessel when said closure is mounted thereon.

2. The closure according to claim 1, wherein said cover is pivotable in a plane substantially perpendicular to the axis of said cylindrical member and further comprises retaining members formed on respective parts of said cylindrical member and said cover and adapted to keep said cover in said closed position.

3. The closure according to claim 1, further comprising retaining members formed on respective parts of said cylindrical member and said cover and adapted to keep said cover in said closed position.

4. The closure according to claim 1, wherein said cover is pivotable in an arc substantially in a plane which is parallel to the axis of said cylindrical member.

5. The closure according to claim 4, further comprising retaining members formed on respective parts of said cylindrical member and said cover and adapted to keep said cover in said closed position.

6. A fermentation vessel adapted for use in an aerobic procedure, comprising:
    (a) a molded substantially hollow body with a cylindrical neck portion having an open top;
    (b) a plurality of radial connecting members integrally formed on the exterior of said cylindrical neck portion;
    (c) a cylindrical tubular member integrally formed concentric with said neck portion and being connected thereto by said radial connecting members;
    (d) a cover pivotably attached to said cylindrical tubular member adjacent said open top so as to be moveable between a closed position and an open position; and
    (e) means to support said cover so that a space is maintained between said cover and an upper end of said vessel neck so as to allow a gas to freely pass between the interior and the exterior of said vessel.

7. The vessel according to claim 6, wherein said cover is pivotable in a plane substantially perpendicular to the axis of said cylindrical member.

8. The vessel according to claim 7, further comprising retaining members formed on respective parts of said cylindrical member and said cover and adapted to keep said cover in said closed position.

9. The vessel according to claim 6, wherein said cover is pivotable in an arc residing in a plane which is substantially parallel to the axis of said cylindrical member.

10. The vessel according to claim 9, further comprising retaining members formed on respective parts of said cylindrical member and said cover and adapted to keep said cover in said closed position.

11. A closure for a fermentation vessel adapted for use in either an aerobic or an anaerobic procedure, said closure comprising:
    (a) a cylindrical tubular member with a first and a second open end and having an inside diameter adjacent said first open end greater than the outside diameter of the neck of a vessel on which said cylindrical member is to be mounted;
    (b) a plurality of stand-off members radially spaced around the inside surface of and integrally molded with said cylindrical member and extending radially inwardly to a diameter adapted to fit snugly over the outside diameter or said neck of said vessel;
    (c) a cover pivotably attached to said cylindrical tubular member adjacent said second open end so as to be moveable between a closed position and an open position in which said cover resides remote from said second open end;
    (d) means to releasably support said cover so that a space is maintained between said cover and an upper end of said vessel neck so as to allow a gas to freely pass between the interior and the exterior of said vessel; and
    (e) sealing means formed integrally with said cylindrical tubular member and positioned so that when said support means maintains a space for gas flow between the interior and the exterior of said vessel said sealing means does not contact the neck of said vessel and when said support means does not maintain said space, said sealing means contacts the neck of said vessel and prevents such gas flow.

12. The closure according to claim 11, wherein said cover is pivotable in an arc substantially in a plane which is parallel to the axis of said cylindrical member.

13. The closure according to claim 12, further comprising retaining members formed on respective parts of said cylindrical member and said cover and adapted to keep said cover in said closed position.

14. A fermentation vessel adapted for use in an aerobic procedure, comprising:
    (a) a molded substantially hollow body with a cylindrical neck portion having an open top;
    (b) a plurality of spaced apart radial connecting members integrally formed on the exterior of said cylindrical neck portion;

(c) a first portion of a cylindrical tubular member integrally formed concentric with and of a greater diameter than said neck portion and being connected thereto by said radial connecting members;

(d) a second portion of a cylindrical tubular member formed complementary to said first portion and integral with a disk-like cover at an upper end of the inner diameter thereof; and (e) each said cylindrical tubular member portion being formed with reciprocal means to adapt said second portion to pivot with relation to said first portion so as to form a complete closure and retain a space for gas to flow between the interior and exterior of said vessel.

* * * * *